US012594287B2

(12) United States Patent
Wang et al.

(10) Patent No.: US 12,594,287 B2
(45) Date of Patent: Apr. 7, 2026

(54) HUMAN MILK OLIGOSACCHARIDE FOR IMPROVING HEALTH OF INTESTINAL MICROENVIRONMENT AND USE THEREOF

(71) Applicants: Inner Mongolia Yili Industrial Group Co., Ltd., Hohhot City (CN); INNER MONGOLIA DAIRY TECH RES INSTITUTE CO LTD, Hohhot City (CN)

(72) Inventors: Wendan Wang, Hohhot City (CN); Ignatius Man-Yau Szeto, Hohhot City (CN); Biao Liu, Hohhot City (CN)

(73) Assignees: Inner Mongolia Yili Industrial Group Co., Ltd., Hohhot City (CN); Inner Mongolia Dairy Tech Res Institute Co Ltd, Hohhot City (CN)

( * ) Notice: Subject to any disclaimer, the term of this patent is extended or adjusted under 35 U.S.C. 154(b) by 487 days.

(21) Appl. No.: 18/006,776

(22) PCT Filed: Jan. 27, 2021

(86) PCT No.: PCT/CN2021/073914
§ 371 (c)(1),
(2) Date: Jan. 25, 2023

(87) PCT Pub. No.: WO2022/110542
PCT Pub. Date: Jun. 2, 2022

(65) Prior Publication Data
US 2023/0285431 A1     Sep. 14, 2023

(30) Foreign Application Priority Data

Nov. 30, 2020     (CN) .......................... 202011376923.9

(51) Int. Cl.
| | |
|---|---|
| *A61K 31/702* | (2006.01) |
| *A23L 33/00* | (2016.01) |
| *A23L 33/125* | (2016.01) |
| *A61K 9/00* | (2006.01) |
| *A61K 35/20* | (2006.01) |
| *A61P 1/14* | (2006.01) |

(52) U.S. Cl.
CPC .......... *A61K 31/702* (2013.01); *A23L 33/125* (2016.08); *A23L 33/40* (2016.08); *A61K 9/0056* (2013.01); *A61K 35/20* (2013.01); *A61P 1/14* (2018.01)

(58) Field of Classification Search
CPC .... A61K 31/702; A61K 9/0056; A61K 35/20; A23L 33/125; A23L 33/40; A61P 1/14
USPC ........................................................ 514/61
See application file for complete search history.

(56) References Cited

U.S. PATENT DOCUMENTS

| | | | |
|---|---|---|---|
| 2012/0171165 A1 | 7/2012 | Buck et al. |
| 2012/0171166 A1 | 7/2012 | Chow et al. |
| 2012/0172319 A1 | 7/2012 | Chow et al. |
| 2014/0037601 A1 | 2/2014 | Greenberg |
| 2014/0335065 A1 | 11/2014 | Davis et al. |
| 2014/0335066 A1 | 11/2014 | Mikelsaar et al. |
| 2018/0220690 A1 | 8/2018 | Berger et al. |
| 2019/0029302 A1 | 1/2019 | Binia et al. |
| 2019/0046545 A1 | 2/2019 | Binia et al. |
| 2020/0101094 A1 | 4/2020 | McConnell et al. |
| 2020/0138836 A1 | 5/2020 | Sprenger et al. |
| 2020/0155580 A1 | 5/2020 | Vigsnæs et al. |
| 2020/0163981 A1 | 5/2020 | Rochat et al. |

FOREIGN PATENT DOCUMENTS

| | | |
|---|---|---|
| CN | 103338775 A | 10/2013 |
| CN | 103402376 A | 11/2013 |
| CN | 103458888 A | 12/2013 |
| CN | 103763940 A | 4/2014 |
| CN | 108495637 A | 9/2018 |
| CN | 108697142 A | 10/2018 |

(Continued)

OTHER PUBLICATIONS

International Search Report for International Application No. PCT/CN2021/073914, "Breast Milk Oligosaccharide for Improving Intestinal Microenvironment Health and Use Thereof", date of mailing: Aug. 5, 2021.

(Continued)

*Primary Examiner* — Yih-Horng Shiao

(74) *Attorney, Agent, or Firm* — Hamilton, Brook, Smith & Reynolds, P.C.

(57) ABSTRACT

The present disclosure provides human milk oligosaccharide for improving the health of intestinal microenvironment and the use thereof. Specifically, the present disclosure provides the use of human milk oligosaccharide, especially the fucosyl-based oligosaccharide 2'-FL or 3-FL in the preparation of a food for improving the health of the intestinal microenvironment, wherein the improving the health of the intestinal microenvironment includes: functioning as prebiotics in the intestinal system that are used by intestinal flora to produce gas, lowering pH to maintain the health of the intestinal microenvironment, and/or reducing branched chain fatty acids such as isobutyric acid and/or isovaleric acid. The human milk oligosaccharide of the present disclosure is used to be added into infant foods (including infant formula powder, supplementary food, and nutritional supplements), and nutritional supplements or foods for children at the age of 3 years or older, adolescents and adults, and has broad application prospects.

9 Claims, 9 Drawing Sheets

(56)                    References Cited

FOREIGN PATENT DOCUMENTS

| CN | 108741083 A | 11/2018 |
|----|-------------|---------|
| CN | 110621168 A | 12/2019 |
| CN | 110650635 A | 1/2020 |
| CN | 110839702 A | 2/2020 |
| CN | 111838683 A | 10/2020 |
| RU | 2018107583 A | 9/2019 |
| WO | 2018215960 A1 | 11/2018 |
| WO | 2018215961 A1 | 11/2018 |
| WO | WO 2019/101489 * | 5/2019 |
| WO | 2020097443 A1 | 5/2020 |
| WO | 2020239996 A1 | 12/2020 |
| WO | 2020245313 A1 | 12/2020 |

OTHER PUBLICATIONS

Thompson-Chagoyan, O.C., et al., "Faecal Microbiota and Short-Chain Fatty Acid Levels in Faeces from Infants with Cow's Milk Protein Allergy", Int. Arch Allergy Immunol 2011; 156-325-332.

Heimann, E., et al., "Branched short-chain fatty acids modulate glucose and lipid metabolism in primary adipocytes", 25 pages. 2016.

Szczesniak, O., et al., "Isovaleric acid in stool correlates with human depression", 2016, 5 pages.

Aguirre, M., et al., "Diet drives quick changes in the metabolic activity and composition of human gut microbiota in a validated in vitro gut model", Research in Microbiology, 2015, 12 pages.

Bridgman, S.L., et al., "Fecal Short-Chain Fatty Acid Variations by Breastfeeding Status in Infants at 4 months: Differences in Relative versus Absolute Concentrations", Frontiers in Nutrition, 4(11): Apr. 2017, 12 pages.

Xie, J-L et al., Human Gut Microbes Degrade and Utilize Fucoidan and Itsigosaccharides From Laminaria Japonica in Vitro, Oceanologia et Limnologia Sinica, vol. 48 No. 1, 2017, 7 pages.

Chinese Search Report for Chinese Application No. 2020113769239, "Human milk oligosaccharides capable of Improving intestinal microenvironment health and application of human milk oligosaccharides" Sep. 10, 2021.

Supplementary Chinese Search Report for Chinese Application No. 2020113769239, "Human milk oligosaccharides capable of improving intestinal microenvironment health and application of human milk oligosaccharides" Dec. 22, 2021.

Salli, K. et al., "The effect of 2-fucosyllactose on simulated infant gut microbiome and metabolites; a pilot study in comparison to GOS and lactose", Scientific Reports, 2019, vol. 9 article 13232.

Li, A-L et al., "Effect of 2'-fucosyllactose supplementation on intestinal flora in mice with intestinal inflammatory diseases", 2020, International Dairy Journal vol. 110, article 104797.

Donovan, S. et al., "Human Milk Oligosaccharides Influence Neonatal Mucosal and Systemic Immunity",2016, Ann Nutr Metab vol. 69.

Van den Elsen et al., "Prebiotic oligosaccharides in early life alter gut microbiome development in male mice while supporting influenza vaccination responses", 2019, Beneficial Microbes, vol. 10, No. 3.

Rios-Covian D. et al., "An Overview on Fecal Branched Short-Chain Fatty Acids Along Human Life and as Related With Body Mass Index: Associated Dietary and Anthropometric Factors", 2020, Frontiers in Microbiology, vol. 11, Article 973.

Heimann, E. et al., "Branched short-chain fatty acids modulate glucose and lipid metabolism in primary adipocytes", 2016, Adipocyte, vol. 5, issue 4-.

International Preliminary Report on Patentability for International Application No. PCT/CN2021/073914, "Breast Milk Oligosaccharide for Improving Intestinal Microenvironment Health and use Thereof", dated May 30, 2023.

Z.T Yu et al, The principal fucosylated oligosaccharides of human milk exhibit prebiotic properties on cultured infant microbiota, Glycobiology, vol. 23 No. 2, pp. 169-177, 2013.

Šuligoj, T. et al., Effects of Human Milk Oligosaccharides on the Adult Gut Microbiota and Barrier Function, Nutrients, vol. 12 No. 9 (2020).

Supplementary European Search Report for EP Application No. 21896062, Breast Milk Oligosaccharide for Improving Intestinal Microenvironment Health and use Thereof, dated Sep. 12, 2024.

Written Opinion for International Application No. PCT/CN2021/073914, "Breast Milk Oligosaccharide for Improving Intestinal Microenvironment Health and use Thereof", date of mailing: Aug. 5, 2021.

* cited by examiner

| infant SHIME | First set | Second set | Third set |
|---|---|---|---|
| First batch | Control | 2'-FL | 3-FL |
| Second batch | LNT | 3'-SL | 6'-SL |

| Yili_PC_feb-... | Yili_DC_feb... | Family (Aggregated) |
|---:|---:|---|
| 1 | 3146 | Burkholderiaceae |
| 11261 | 35 | Clostridiaceae 1 |
| 1290 | 413 | Enterobacteriaceae |
| 215 | 551 | Enterococcaceae |
| 1 | 960 | Erysipelotrichaceae |
| 0 | 18 | Fusobacteriaceae |
| 8 | 9943 | Lachnospiraceae |
| 16 | 1 | Mitochondria |
| 17 | 1 | Moraxellaceae |
| 2 | 0 | Peptostreptococcaceae |
| 760 | 64 | Pseudomonadaceae |
| 2555 | 354 | Veillonellaceae |
| 268 | 22 | Xanthomonadaceae |

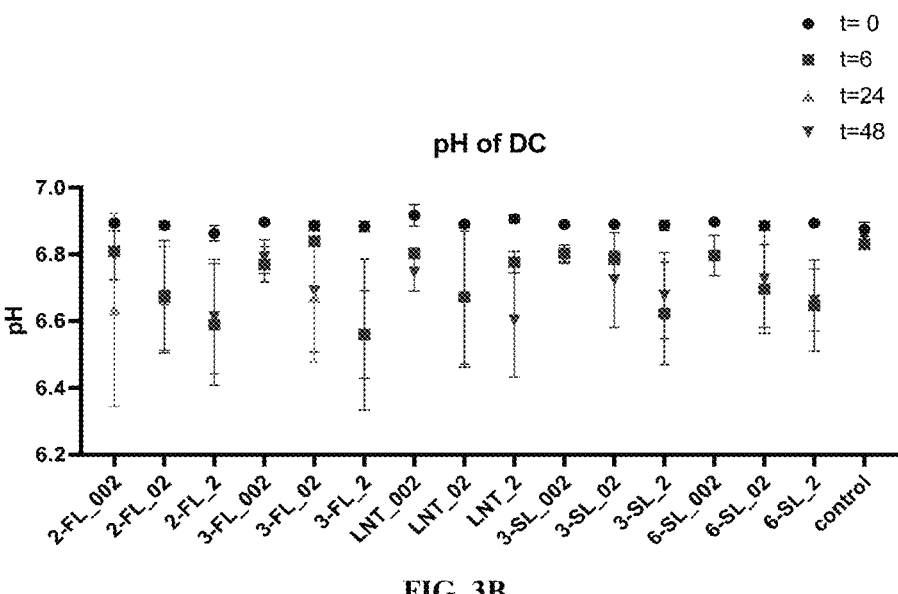
FIG. 3B
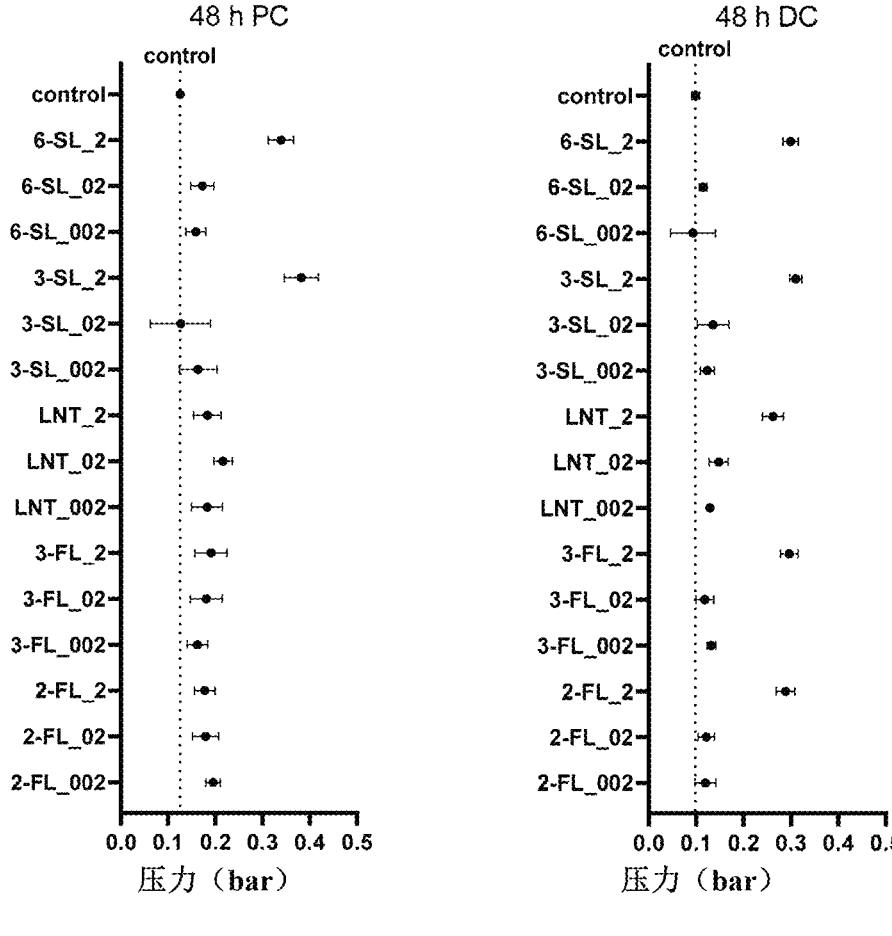
FIG. 4A                                   FIG. 4B

P-value ≤ 0.05:   *
P-value ≤ 0.01:   **
P-value ≤ 0.001: ***

DC_Yili

Legend:
- Iso-valeric acid
- Iso-butyric acid
- Formic acid
- Lactic acid
- Butyric acid
- Propionic acid
- Acetic acid mM total SCFA DC

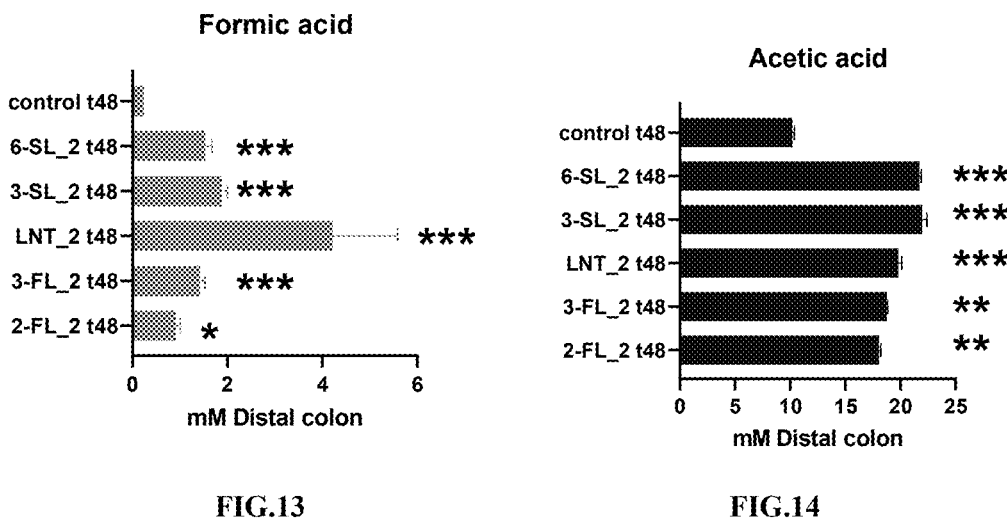
FIG.13
FIG.14
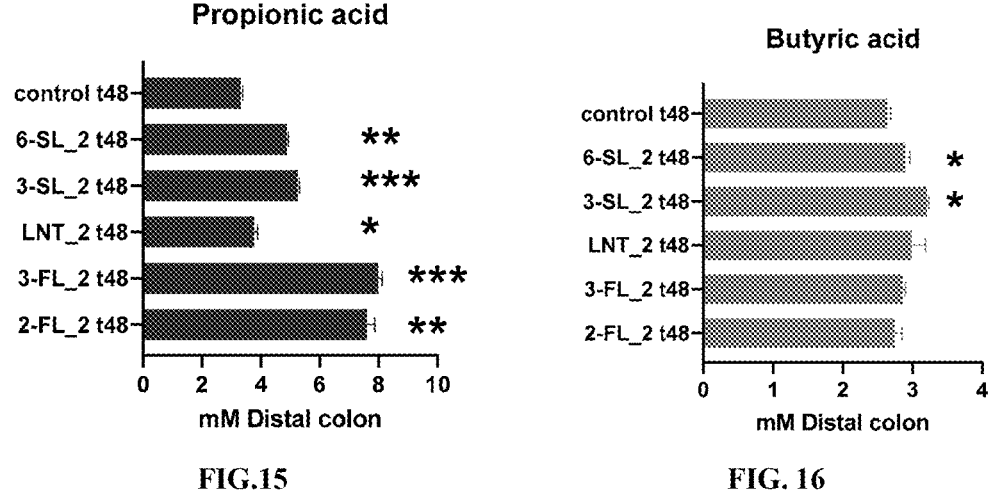
FIG.15
FIG. 16

HUMAN MILK OLIGOSACCHARIDE FOR IMPROVING HEALTH OF INTESTINAL MICROENVIRONMENT AND USE THEREOF

This application is the U.S. National Stage of International Application No. PCT/CN2021/073914, filed Jan. 27, 2021, which designates the U.S., published in Chinese, and claims priority under 35 U.S.C. § 119 or 365(c) to Chinese Application No. 202011376923.9, filed Nov. 30, 2020. The entire teachings of the above applications are incorporated herein by reference.

TECHNICAL FIELD

The present disclosure relates to new use of human milk oligosaccharide, specifically, new use of human milk oligosaccharide such as 2'-FL, 3-FL, and 3-SL in the improvement of the health of intestinal microenvironment.

BACKGROUND

Human milk oligosaccharides (Human Milk Oligosaccharides, abbreviated as HMOs) is the third most abundant substance in human milk after lactose and fat. The overall content thereof varies through various stages of lactation and is approximately 12 to 14 g/L in mature milk, and approximately 20 to 24 g/L in colostrum. In the structure of each of human milk oligosaccharides, a lactose is present at the reducing end, and most of them have a polylactosamine skeleton, with fucose, sialic acid or both comprised at the end of the chain. Human milk oligosaccharides are mainly composed of three types: (1) fucosyl-based oligosaccharides, represented by 2'-fucosyl oligosaccharide and 3'-fucosyl oligosaccharide; (2) sialyl-based oligosaccharides, represented by 3'-sialyl lactose and 6'-sialyl lactose; (3) oligosaccharides formed by a core sugar chain structure excluding fucosyl or sialyl, represented by lacto-N-tetraose and lacto-N-neotetraose. The presence and contents of HMOs differ among individuals and are associated with the the Secretor-status and Lewis type of the nursing mother. Since the raw material of infant formula powder is generally cow's milk which often contains little or no such oligosaccharide substances, HMO is a hurdle that must be passed for an infant formula powder to more closely resemble human milk.

Intestinal flora is an important component of the human intestinal microecosystem and plays an important role in human health. Anaerobic bacilli, bifidobacteria, eubacteria, streptococci, lactobacilli in the intestinal flora can produce short chain fatty acids (SCFA), mainly including acetic acid, propionic acid, butyric acid etc., by fermenting carbohydrates, proteins, lipids and the like. SCFA can regulate various physiological activities of the body and also play an important role in regulating the health of the intestinal microenvironment. For example, SCFA can provide energy and regulate electrolytes; acetic acid is an important energy source of the host, propionic acid can participate in the reverse conversion of pyruvate to glucose, and butyric acid is uptaken by epithelial cells and is the main energy source for epithelial cells. SCFA also has anti-inflammatory and intestinal barrier-enhancing function as well as antibacterial effects. SCFA produced by the fermentation of the intestinal flora can reduce the intestinal pH, thereby increasing the growth of beneficial bacteria in the intestine and reducing the proliferation of harmful bacteria.

In addition, there may also be small amounts of branched chain fatty acids (BCFA) such as isobutyric acid and isovaleric acid in intestinal metabolites. These are produced through metabolism of branched chain amino acids such as valine, leucine, and isoleucine by the intestinal flora, and are products from the bacteria fermentation of undigested proteins and polypeptides upon their entry in the colon, mainly derived from diet or shedding of mucosal cells. Therefore, unlike acetic acid, propionic acid and butyric acid, isobutyric acid and isovaleric acid are metabolites of proteins. The reduction in isobutyric acid and isovaleric acid can be considered as a shift from protein fermentation to fiber fermentation, which is believed to be a positive effect. These branched chain fatty acids are regarded as markers of colonic protein fermentation which also produces other metabolites such as ammonia, phenol, p-cresol, or biogenic amines capable of damaging cells in the small intestinal environment (Aguirre et al., 2016). High level of isovaleric acid in feces is associated with depression and cortisol levels in humans (Szczesniak et al., 2016), and studies have recently been done on glucose and lipid metabolism by BCFA (Heimann et al., 2016).

Exclusively breastfed infants have lower levels of isobutyric acid and isovaleric acid measured in their feces compared to those who are not breastfed (Bridgman et al, 2017). High branched chain fatty acids such as valeric acid, isobutyric acid, and isovaleric acid in feces are derived from metabolism of amino acids, and their presence indicates lower protein uptake or excess protein intake in the infant formula-fed group (likely due to the higher protein content in infant formula powder than in human milk). These metabolites may also contribute to higher levels of bacteria responsible for proteolysis, such as *Bacteroides* and *Clostridium*, in the feces of formula-fed infants. The formula-fed infants have higher levels of proteolytic metabolites in their feces, possibly because of a lower presence of carbohydrates due to absence of HMOs in the infant formula powder, and thus these infants rely more on protein metabolism for energy acquisition.

Studies done by Chow et al. also show that when fermentable carbohydrates are absent in the fecal culture system of breast-fed and formula-fed infants, metabolites from protein fermentation are mainly produced; and when various fermentable HMO-like carbohydrates are added, the levels of these protein metabolites are reduced. High levels of short chain fatty acids in the feces of the formula-fed group may have an impact on the metabolism of infants. Several studies have reported that overweight adults and children have increased short chain fatty acids in feces than their lean counterparts, which is associated with other metabolic risk factors. Thompson-Chagoyan et al. (2011) conducted a study on 92 infants at an age of 2-12 months, with half thereof non-allergic to cow's milk proteins and the other half showing allergy symptoms. The concentrations and proportions of branched chain fatty acids in the feces of the infants with allergy to cow's milk proteins were higher than those in healthy infants.

For adults, with deficiency in gastric acid, the protein digestion may be insufficient, and the intestines are prone to produce branched short chain fatty acids. Those short chain fatty acids are formed from undigested branched chain amino acids fermented by anaerobic bacteria, including valeric acid, isovaleric acid, and isobutyric acid. Abnormal elevations of branched short chain fatty acids indicate protein maldigestion, suggesting potential achlorhydria, pancreatic insufficiency, malabsorption, and small intestinal bacterial overgrowth (SIBO). In addition, in cancer research, metabolite analysis of colorectal cancer shows that branched chain amino acids, phenylalanine and the like are significantly increased in the early stages of the disease. Isovaleric acid, a branched chain fatty acid, increases gradually with the progression of the disease.

At present, in the fields of infant formula powder, supplementary food and nutritional supplements, there is a need for solutions that can improve the health of the intestinal microenvironment, for example, by reducing branched chain fatty acids such as isobutyric acid and isovaleric acid. Meanwhile, in the fields of children at the age of 3 years or older, adolescents and adults, it is also necessary to maintain the stability and health of the intestinal microecosystem.

SUMMARY

An object of the present disclosure is to provide a new use of human milk oligosaccharides.

The present inventors discover that some human milk oligosaccharides have an effect of significantly improving the health of the intestinal microenvironment, manifested in functioning as prebiotics in the intestinal system that are used by the intestinal flora to produce gas, lowering pH to maintain the health of the intestinal microenvironment, and reducing branched chain fatty acids such as isobutyric acid and isovaleric acid, which provides a new use of human milk oligosaccharides.

Specifically, the present disclosure provides use of human milk oligosaccharides in the preparation of a food for improving the health of the intestinal microenvironment, wherein the improving the health of the intestinal microenvironment includes: functioning as prebiotics in the intestinal system that are used by the intestinal flora to produce gas, lowering pH to maintain the health of the intestinal microenvironment, and/or reducing branched chain fatty acids.

Known human milk oligosaccharides include fucosyl lactose, sialyl lactose, and basic sugar chain structures of human milk oligosaccharides without fucosyl or sialyl group (typical representative substances include lacto-N-tetraose and its isomer lacto-N-neotetraose).

Among them, 2'-fucosyllactose (2'-FL or 2-FL or 2FL) is a trisaccharide structure formed by fucose and lactose, and is a representative substance of fucosyl-based oligosaccharides. Commercial 2'-fucosyl lactose is generally prepared by microbial fermentation and has the same structure as the oligosaccharide found in human milk.

3-fucosyllactose (3'-FL or 3-FL or 3FL) is a trisaccharide structure formed by fucose and lactose, an isomer of 2'-fucosyl lactose, and a representative substance of fucosyl-based oligosaccharides. It is prepared by microbial fermentation and has the same structure as the oligosaccharide found in human milk.

Lacto-N-tetraose (LNT) is a tetrasaccharide structure formed by lactose, N-acetylglucosamine, and galactose, and is a representative substance of oligosaccharides which have a basic structure with a core sugar chain and no fucosyl or sialyl group. It is prepared by microbial fermentation and has the same structure as the oligosaccharide found in human milk.

3'-sialyl lactose (3'-SL or 3-SL or 3SL) is a trisaccharide structure formed by sialic acid and lactose, and is a representative substance of sialyl-based oligosaccharides. It is prepared by microbial fermentation and has the same structure as the oligosaccharide found in human milk.

6'-sialyl lactose (6'-SL or 6-SL or 6SL) is a trisaccharide structure formed by sialic acid and lactose, and is a representative substance of sialyl-based oligosaccharides. It is prepared by microbial fermentation and has the same structure as the oligosaccharide found in human milk.

According to a specific embodiment of the present disclosure, the use of the human milk oligosaccharides for improving the health of the intestinal microenvironment according to the present disclosure includes: functioning as prebiotics in the intestinal system that are used by the intestinal flora to produce gas, lowering pH to maintain the health of the intestinal microenvironment, and/or reducing branched chain fatty acids.

According to a specific embodiment of the present disclosure, in the use of the human milk oligosaccharide in the preparation of a food for improving the health of the intestinal microenvironment according to the present disclosure, the human milk oligosaccharide is selected from one or more of a fucosyl-based oligosaccharide, a sialyl-based oligosaccharide or lacto-N-tetraose. Preferably, the fucosyl-based oligosaccharide is 2'-FL or 3-FL, and the sialyl-based oligosaccharide is 3-SL or 6-SL.

According to some embodiments of the present disclosure, the human milk oligosaccharides of the present disclosure function as prebiotics by intestinal flora in the proximal colon and produce gas. Preferably, the human milk oligosaccharide is 3-SL, 6-SL or LNT.

According to some embodiments of the present disclosure, the human milk oligosaccharides of the present disclosure function as prebiotics by intestinal flora in the distal colon and produce gas. The human milk oligosaccharide is 2'-FL, 3-FL, 3-SL, 6-SL or LNT.

According to some embodiments of the present disclosure, the human milk oligosaccharides of the present disclosure are used to lower the pH in the proximal colon to maintain the health of the intestinal microenvironment. The human milk oligosaccharide is 2'-FL, 3-FL, 3-SL, 6-SL or LNT.

According to some embodiments of the present disclosure, the human milk oligosaccharides of the present disclosure are used to lower the pH in the distal colon to maintain the health of the intestinal microenvironment. Preferably, the human milk oligosaccharide is 2'-FL, 3-FL or LNT.

According to some embodiments of the present disclosure, the human milk oligosaccharides of the present disclosure are used to reduce the production of branched chain fatty acids in the distal colon.

According to some more specific embodiments of the present disclosure, the human milk oligosaccharides of the present disclosure are used to reduce the production of isobutyric acid in the distal colon. Preferably, the human milk oligosaccharide is 2'-FL, 3-FL, 3-SL or LNT. The food may be milk powder or liquid milk, preferably infant formula powder. When used for this purpose, for example, in the case where the food is infant formula powder, the amount of 2'-FL used in the food is 14.2 mg/100 g powder to 3182.2 mg/100 g powder in the milk powder, or 0.02 g/L to 4.2 g/L in terms of liquid milk; preferably 70.9 mg/100 g powder to 1818.4 mg/100 g powder, or 0.1 g/L to 2.4 g/L in terms of liquid milk; more preferably 70.9 mg/100 g powder to 1515.3 mg/100 g powder, or 0.1 g/L to 2.0 g/L in terms of liquid milk. For example, in the case where the food is infant formula powder, the amount of 3-FL used in the food is 14.2 mg/100 g powder to 1515.3 mg/100 g powder in the milk powder, or 0.02 g/L to 2.0 g/L in terms of liquid milk; preferably 70.9 mg/100 g powder to 1515.3 mg/100 g powder, or 0.1 g/L to 2.0 g/L in terms of liquid milk; more preferably 70.9 mg/100 g powder to 757.7 mg/100 g powder, or 0.1 g/L to 1.0 g/L in terms of liquid milk. For example, in the case where the food is infant formula powder, the amount of 3-SL used in the food is 14.2 mg/100 g powder to 1515.3 mg/100 g powder in the milk powder, or 0.02 g/L to 2.0 g/L in terms of liquid milk; preferably 70.9 mg/100 g powder to 454.6 mg/100 g powder, or 0.1 g/L to 0.6 g/L in terms of liquid milk; more preferably 70.9 mg/100 g powder to 227.3 mg/100 g powder, or 0.1 g/L to 0.3 g/L in terms of liquid milk. For example, in the case where the food is infant formula powder, the amount of LNT used in the food is 14.2 mg/100 g powder to 2273.0 mg/100 g powder in the milk powder, or 0.02 g/L to 3.0 g/L in terms of liquid milk; preferably 70.9 mg/100 g powder to 1515.3 mg/100 g powder, or 0.1 g/L to 2.0 g/L in terms of liquid milk; more preferably 70.9 mg/100 g powder to 757.7 mg/100 g powder, or 0.1 g/L to 1.0 g/L in terms of liquid milk. When the food is another food product, the amount of each human milk oligosaccharide can be adjusted with reference to the above ranges.

According to some more specific embodiments of the present disclosure, the human milk oligosaccharides of the present disclosure are used to reduce the production of isovaleric acid in the distal colon. Preferably, the human milk oligosaccharide is 2'-FL, 3-FL, 3-SL or 6-SL. The food may be milk powder or liquid milk, preferably infant formula powder. When used for this purpose, for example, in the case where the food is infant formula powder, the amount of 2'-FL used in the food is 14.2 mg/100 g powder to 3182.2 mg/100 g powder in the milk powder, or 0.02 g/L to 4.2 g/L in terms of liquid milk; preferably 70.9 mg/100 g powder to 1818.4 mg/100 g powder, or 0.1 g/L to 2.4 g/L in terms of liquid milk; more preferably 70.9 mg/100 g powder to 1515.3 mg/100 g powder, or 0.1 g/L to 2.0 g/L in terms of liquid milk. For example, in the case where the food is infant formula powder, the amount of 3-FL used in the food is 14.2 mg/100 g powder to 1515.3 mg/100 g powder in the milk powder, or 0.02 g/L to 2.0 g/L in terms of liquid milk; preferably 70.9 mg/100 g powder to 1515.3 mg/100 g powder, or 0.1 g/L to 2.0 g/L in terms of liquid milk; more preferably 70.9 mg/100 g powder to 757.7 mg/100 g powder, or 0.1 g/L to 1.0 g/L in terms of liquid milk. For example, in the case where the food is infant formula powder, the amount of 3-SL used in the food is 14.2 mg/100 g powder to 1515.3 mg/100 g powder in the milk powder, or 0.02 g/L to 2.0 g/L in terms of liquid milk; preferably 70.9 mg/100 g powder to 454.6 mg/100 g powder, or 0.1 g/L to 0.6 g/L in terms of liquid milk; more preferably 70.9 mg/100 g powder to 227.3 mg/100 g powder, or 0.1 g/L to 0.3 g/L in terms of liquid milk. For example, in the case where the food is infant formula powder, the amount of 6-SL used in the food is 14.2 mg/100 g powder to 1515.3 mg/100 g powder in the milk powder, or 0.02 g/L to 2.0 g/L in terms of liquid milk; preferably 70.9 mg/100 g powder to 606.1 mg/100 g powder, or 0.1 g/L to 0.8 g/L in terms of liquid milk; more preferably 70.9 mg/100 g powder to 454.6 mg/100 g powder, or 0.1 g/L to 0.6 g/L in terms of liquid milk. When the food is another food product, the amount of each human milk oligosaccharide can be adjusted with reference to the above ranges.

According to a specific embodiment of the present disclosure, in the use of the human milk oligosaccharide in the preparation of a food for improving the health of the intestinal microenvironment according to the present disclosure, the human milk oligosaccharide is also favorable for promoting the production of short chain fatty acids which are beneficial to the body such as formic acid, acetic acid, propionic acid, and butyric acid in the intestinal system. Thus, the improving the health of the intestinal microenvironment according to the present disclosure further includes regulating the production of beneficial short chain fatty acids in the intestinal system, wherein the beneficial short chain fatty acids include formic acid, acetic acid, propionic acid and/or butyric acid.

According to a specific embodiment of the present disclosure, in the use of the human milk oligosaccharide in the preparation of a food for improving the health of the intestinal microenvironment according to the present disclosure, the food includes one or more of a nutritional supplement, an infant formula powder, and a supplementary food. Specifically, the food may be infant food (including infant formula powder, supplementary food, and nutritional supplements), or nutritional supplements or food for children at the age of 3 years or older, adolescents and adults, such as fermented dairy products (such as fermented milk, flavored fermented milk, fermented milk beverages, etc.), cheese, milk-containing beverages, solid beverages, milk powder, or the like.

Above all, the present disclosure provides a discovery that human milk oligosaccharides can significantly improve the health of the intestinal microenvironment, and can be added into infant food (including infant formula powder, supplementary food, and nutritional supplements), and nutritional supplements or food for children at the age of 3 years or older, adolescents and adults, and has broad application prospects.

BRIEF DESCRIPTION OF DRAWINGS

FIG. 3B shows the results from the detection of pH changes in the distal colon over time in the small batch fermentation experiment with each HMO in Example 2 of the present disclosure.

FIG. 4A shows the results from the detection of pressure changes over time resulted in the proximal colon in the small batch fermentation experiment with each HMO in Example 3 of the present disclosure.

FIG. 4B shows the results from the detection of pressure changes over time resulted in the distal colon in the small batch fermentation experiment with each HMO in Example 3 of the present disclosure.

FIG. 13 shows the results from the detection of formic acid produced in a fecal batch fermentation experiment with each human milk oligosaccharide alone in a simulated infant distal colon in Example 7 of the present disclosure.

FIG. 14 shows the results from the detection of acetic acid produced in a fecal batch fermentation experiment with each human milk oligosaccharide alone in a simulated infant distal colon in Example 7 of the present disclosure.

FIG. 15 shows the results from the detection of propionic acid produced in a fecal batch fermentation experiment with each human milk oligosaccharide alone in a simulated infant distal colon in Example 7 of the present disclosure.

FIG. 16 shows the results from the detection of butyric acid produced in a fecal batch fermentation experiment with each human milk oligosaccharide alone in a simulated infant distal colon in Example 7 of the present disclosure.

DETAILED DESCRIPTION

For a clearer understanding of the technical features, purposes and beneficial effects of the present disclosure, the technical solutions of the present disclosure are described below in details in conjunction with specific examples, and it should be understood that these examples are only used to illustrate the present disclosure and not to limit the scope thereof. In the examples, the raw reagents and materials are respectively commercially available, and the experimental methods without particularly specified conditions are conventional methods with conventional conditions well known in the art, or according to the conditions recommended by the instrument manufacturer.

In addition, in order to avoid repetition, the general steps that the experiments in each example need to go through, such as inoculation and culture of fecal bacteria, are listed below.

Fecal Inoculation and Culture in SHIME Device

Figure 1A:
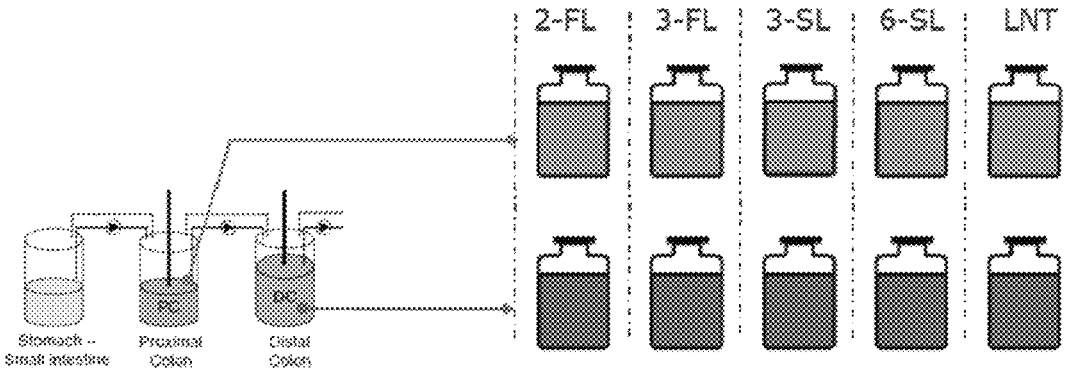
FIG. 1A is a schematic diagram of fecal inoculation and culture in the SHIME device of the present disclosure.

Using a SHIME device (see the schematic diagram in FIG. 1A), fresh fecal samples containing bacteria flora were obtained from a healthy 5-month-old infant naturally delivered and exclusively breastfed, and inoculated into containers corresponding to the proximal colon and distal colon. Food material was fed to the stomach/small intestine end of the device three times a day for two weeks to support the growth and colonization of the flora in the proximal colon and distal colon. Here, the food material that was digested by the small intestine and entered the colon was prepared on the basis of the standard food material provided by ProDigest, the manufacturer of the SHIME device, with adjustment to the ratio of lactose, casein and whey protein; the standard food material was composed of: pectin (1 g/L), glucose (1 g/L), starch (1 g/L), cellobiose (1 g/L), proteose peptone (2 g/L), mucin (6 g/L)), lactose (2.1 g/L), casein (0.2 g/L), whey-lactalbumin (2.7 g/L), L-cysteine hydrochloride (0.2 g/L). The ratio of lactose, casein and whey protein in the food materials in each experiment of the present disclosure was adjusted to about 12:1:15, with reference to Le Blay et al. (2010), and stable and balanced nutrients were maintained, so as to simulate the food composition to which the infant's intestinal microecology may be exposed during regular breastfeeding or infant formula feeding. After the infant fecal flora was stabilized in the SHIME model for two weeks, the proximal colon and distal colon were sampled, aliquoted in glycerol to form a stock solution, and stored under anaerobic conditions at −80° C.

Analysis and detection of the composition of the bacteria flora will be focused on specific strains: *Lactobacillus, Bifidobacterium, Rosetella, Eubacterium* and *Faecalibacterium*, as they are known to be associated with (prebiotic) health benefits. Detection and analysis are based on qPCR.

Small Batch Fermentation

After the infant flora was inoculated into the SHIME model and stably grown for 2 weeks (as described in the aforementioned "Fecal inoculation and culture in SHIME device"), 10 mL of the flora in the proximal colon and distal colon was taken and respectively transferred to fermentation flasks under anaerobic conditions for small batch fermentation. On the basis of 43 mL basal buffer (for adjusting pH and simulating the corresponding colonic environment), each fermentation flask also contained 20 mL PBS buffer (for dissolving and introducing the HMO test substance) supplemented with different amounts of HMOs, so that the final concentration of each HMO was 0.02 g/L, 0.2 g/L, or 2 g/L, the pH of the proximal colon was set to 5.6, and the pH of the distal colon was set to 6.5. The flasks were incubated at 37° C. with shaking. During incubation, the pressure was measured at 0, 6 hours, 24 hours and 48 hours, followed by sampling for detection of pH and short chain fatty acids. Measurements were repeated three times.

During the HMO intervention, the gas production in each group was compared by measuring changes in pressure. Short chain fatty acid analysis including isobutyric acid, isovaleric acid, butyric acid, propionic acid, acetic acid, and formic acid, were analyzed by HPLC.

SHIME Fermentation

Figure 1B:
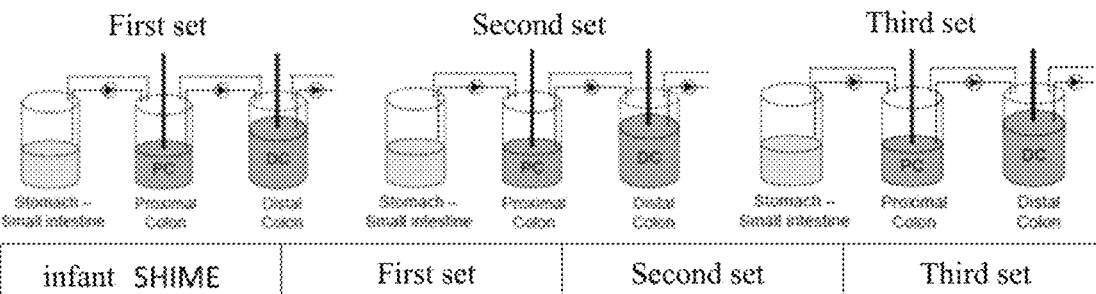
FIG. 1B shows a schematic diagram of the SHIME fermentation grouping of the present disclosure.

The infant fecal flora sampled and stored as in "Fecal inoculation and culture in SHIME device" was inoculated into the SHIME model to investigate the fermentation of HMOs in the SHIME device. Two batches of experiments were done sequentially, and three sample groups (or control) were simultaneously done in each batch of experiments. In three sets of experimental devices, the devices simulating the proximal colon and distal colon were inoculated separately (see the schematic diagram of FIG. 1B). Food material was fed three times a day, and after 4 days of incubation, an HMO was blended into the feed food material (no HMO was added to the control group). 280 mg of HMO (at a concentration of 2 g/L) and 60 mL of pancreatic juice were added into 140 mL of a stock solution for each food material. Only one experiment was performed for each set of HMO and control, so the biological replicate was 1. SHIME fermentation continued until Day 14 after the HMO intervention, and samples were taken for detection at different time periods during the fermentation period.

Data Analysis

A two-tailed, paired t-test was performed on the data results. When there is a significant difference between two groups, and $p<0.05$, it is indicated with an asterisk *. Two asterisks  indicate $p<0.01$. Three asterisks * indicate $p<0.001$.

Example 1: Bacteria Flora in Simulated Proximal and Distal Colonic Environments Reference is made to the preceding paragraphs for the pre-experimental preparation steps and specific experimental methods.

Figure 2:
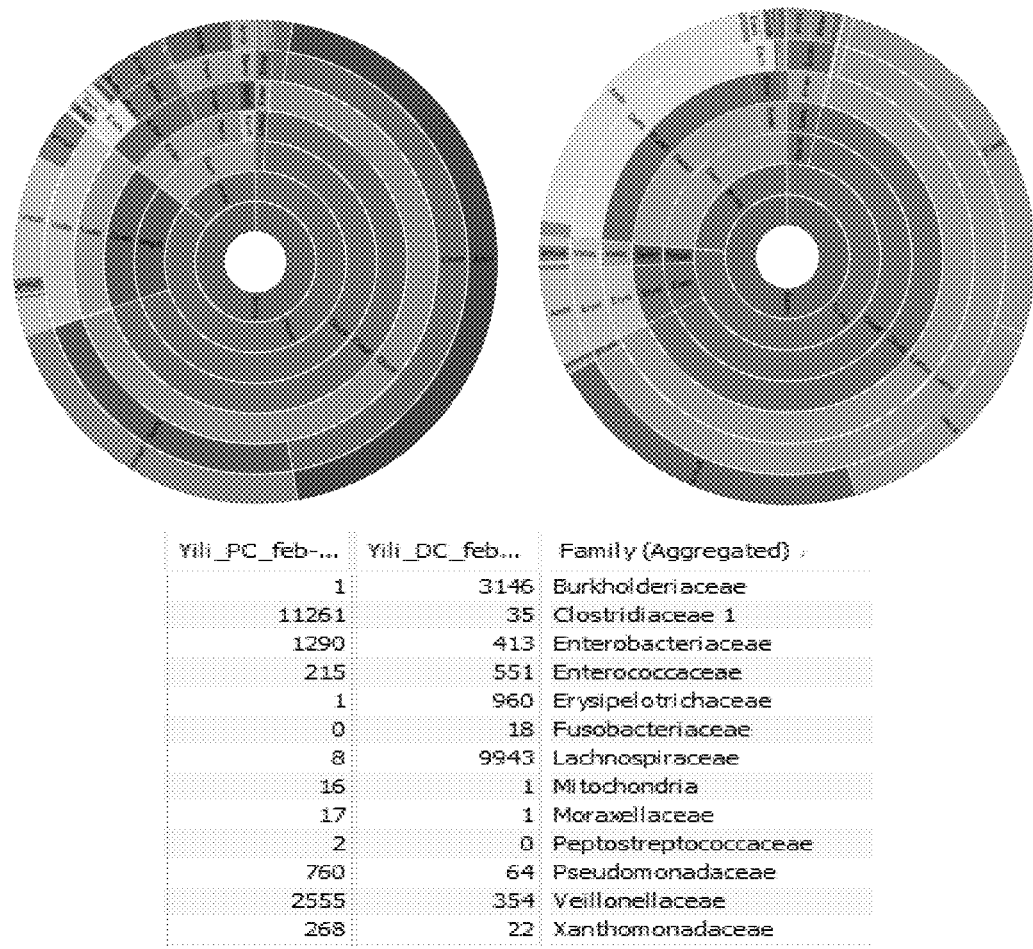
FIG. 2 shows the flora in the simulated proximal colon (left) and distal colon (right) after two weeks of culture in the SHIME device that simulates an infant colon.

Reference is made to FIG. 2 for the identification of fecal flora after two weeks of inoculation, culture and stabilization in the SHIME device. After stabilization in the SHIME model for two weeks, it was found by flora determination that the contents of *Bifidobacterium* and *Lactobacillus* were extremely low and even undetectable, which was consistent with the previous report in the literature (Laforest-Lapointe, 2017). It was demonstrated that in a simulated infant intestinal environment, the flora environment of the corresponding colon was closer to formula-fed infants rather than breast-fed infants, after feeding with the standard food material containing lactose/casein/whey protein.

Example 2: PH Changes Over Time in Small Batch Fermentation Experiments with Each HMO Reference is made to the preceding paragraphs for the pre-experimental preparation steps and specific experimental methods.

Figure 3A:
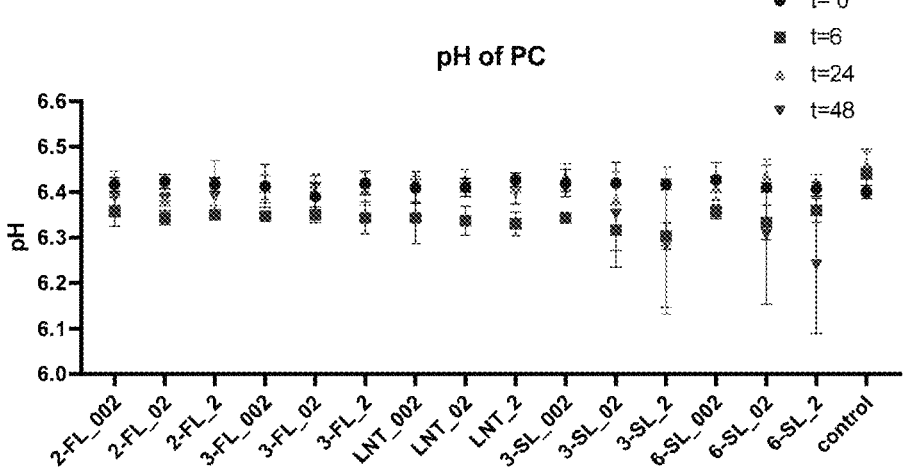
FIG. 3A shows the results from the detection of pH changes in the proximal colon over time in the small batch fermentation experiment with each HMO in Example 2 of the present disclosure.

Reference is made to FIG. 3A for the detection results of pH changes of the proximal colon over time in the small batch fermentation experiment with each HMO. Reference is made to FIG. 3B for the detection results of pH changes of the distal colon over time in the small batch fermentation experiment with each HMO. It can be seen that in the proximal colon, the pH reduction at 6 hours is more pronounced than at other time points. In the distal colon, 2 g/L of 2'-FL and 3-FL tend to significantly lower the pH. It can be seen that as the fermentation time increases, HMO is utilized by the bacteria flora in the infant feces to produce short chain fatty acids, thereby lowering the pH. LNT tends to better lower the pH at 0.2 g/L.

Example 3: Pressure Changes Over Time in Small Batch Fermentation Experiments with Each HMO Reference is made to the preceding paragraphs for the pre-experimental preparation steps and specific experimental methods.

Reference is made to FIG. 4A for the detection results of pressure changes over time resulted in the proximal colon in the small batch fermentation experiment with each HMO. Reference is made to FIG. 4B for the detection results of pressure changes over time resulted in the distal colon in the small batch fermentation experiment with each HMO. It can be seen that the two sialyl-based oligosaccharide, 3-SL and 6-SL, result in higher pressure in the proximal colon at 2 g/L, which demonstrates that under this condition these two oligosaccharides can be better utilized by the fecal flora. At 0.2 g/L, LNT tends to produce gas better. In the simulated distal colon, all HMOs resulted in an increase in air pressure at 2 g/L.

Figure 5A:
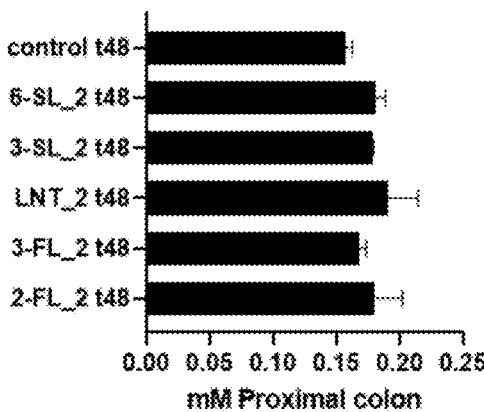
FIG. 5A shows the results from the detection of isobutyric acid produced by small batch fermentation with each HMO in a simulated proximal colon environment in Example 4 of the present disclosure.
Figure 5B:
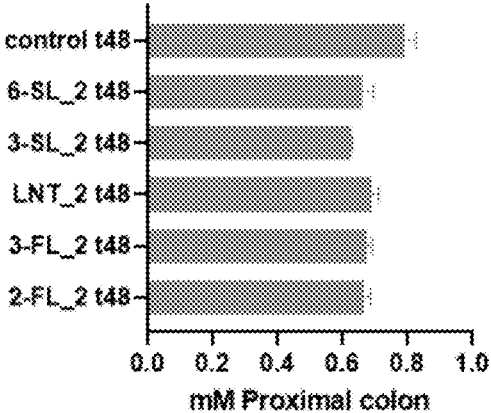
FIG. 5B shows the results from the detection of isovaleric acid produced by small batch fermentation with each HMO in a simulated proximal colon environment in Example 4 of the present disclosure.

Example 4: Production of Isobutyric Acid and Isovaleric Acid by Small Batch Fermentation With Each HMO in the Simulated Proximal Colon Environment Short chain fatty acids (SCFAs) such as isobutyric acid and isovaleric acid are mainly produced by protein fermentation. Reference is made to FIG. 5A and FIG. 5B respectively for the detection results of isobutyric acid and isovaleric acid produced by small batch fermentation with each HMO in a simulated proximal colon environment in the present disclosure. It can be seen that each HMO does not affect the production of isobutyric acid and isovaleric acid in small batch fermentations in the simulated proximal colon.

Figure 6A:
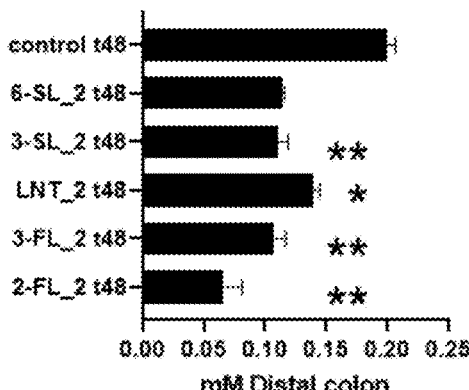
FIG. 6A shows the results from the detection of isobutyric acid produced by small batch fermentation with each HMO in a simulated distal colon environment in Example 4 of the present disclosure.
Figure 6B:
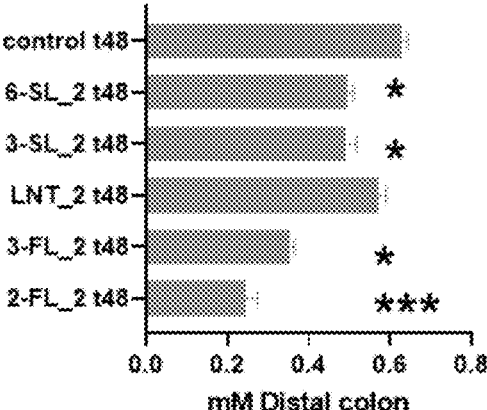
FIG. 6B shows the results from the detection of isovaleric acid produced by small batch fermentation with each HMO in a simulated distal colon environment in Example 4 of the present disclosure.

Example 5: Production of Isobutyric Acid and Isovaleric Acid by Small Batch Fermentation with Each HMO in the Simulated Distal Colon Environment Reference is made to FIG. 6A and FIG. 6B respectively for the detection results of isobutyric acid and isovaleric acid produced by small batch fermentation with each HMO in a simulated distal colon environment. It can be seen that in the distal colon, 2'-FL, 3-FL, 3-SL, and LNT can significantly reduce the production of isobutyric acid, with the two fucosyl-based oligosaccharides having a better effect. Both sialyl-based oligosaccharides and fucosyl-based oligosaccharides can reduce the production of isovaleric acid, with 2'-FL being most potent. Overall, the two fucosyl-based oligosaccharides, 2'-FL and 3-FL, can significantly reduce the production of isobutyric acid and isovaleric acid.

Figure 7:
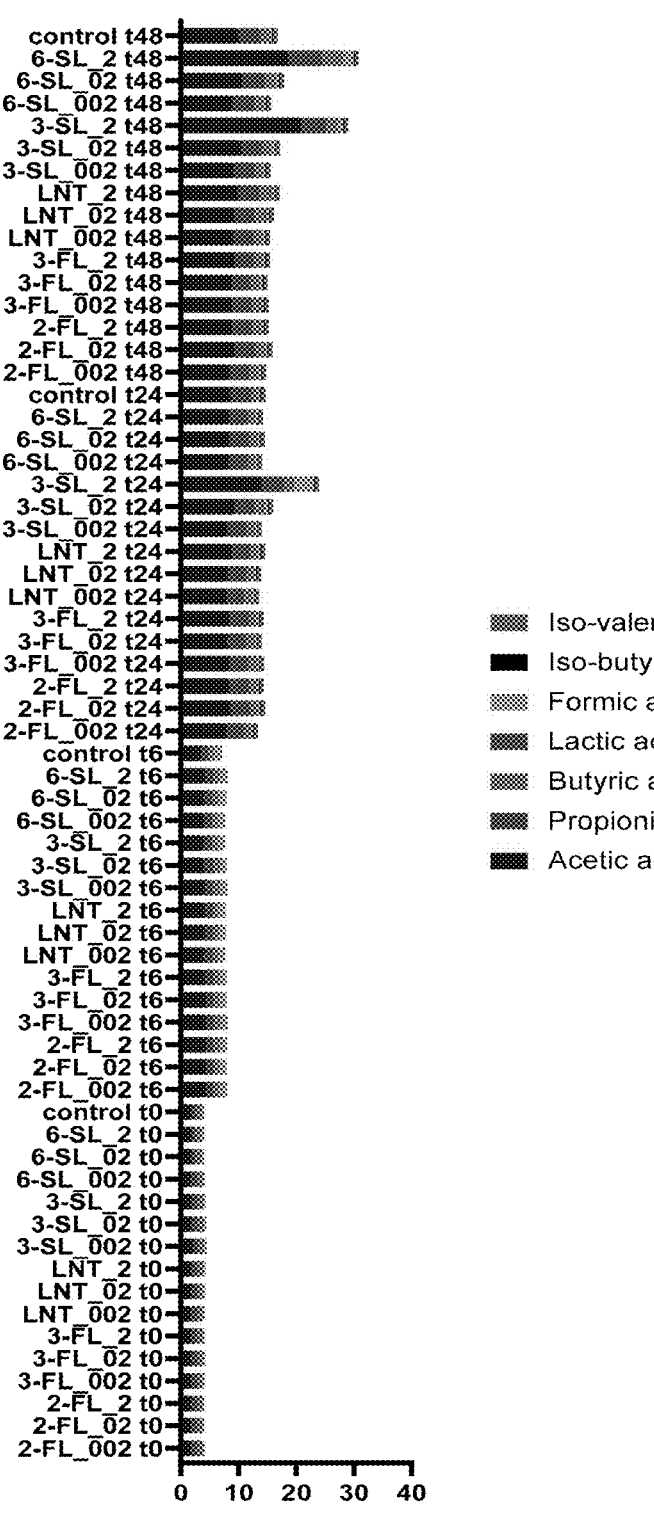
FIG. 7 shows the overall results from the detection of short chain fatty acids produced by small batch fermentation with each HMO in a simulated proximal colon environment in Example 6 of the present disclosure.

Example 6: Production of Short Chain Fatty Acids by Small Batch Fermentation with Each HMO in the Simulated Proximal Colon Environment Reference is made to FIG. 7 for the total detection results of short chain fatty acids produced by small batch fermentation with each HMO in a simulated proximal colon environment. It can be seen that after 48 hours of fermentation with all HMOs, the short chain fatty acids produced are higher than those at other time points. Among them, 3-SL and 6-SL produce significantly more SCFA at 2 g/L, whereas 3-SL at 2 g/L also produces more SCFA after 24 hours of fermentation.

Figure 8:
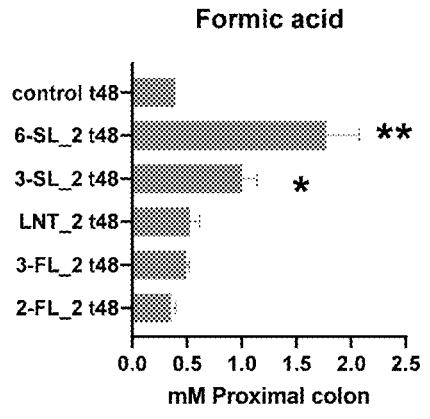
FIG. 8 shows the results from the detection of formic acid produced in a fecal batch fermentation experiment with each human milk oligosaccharide alone in a simulated infant proximal colon in Example 6 of the present disclosure.

Reference is made to FIG. 8 for the detection results of formic acid produced by small batch fermentation with each HMO in a simulated proximal colon environment. It can be seen that 3-SL and 6-SL have significantly increased formic acid after 48 hours of fermentation in the simulated proximal colon. Among them, the effect of 6-SL is more significant.

Figure 9:
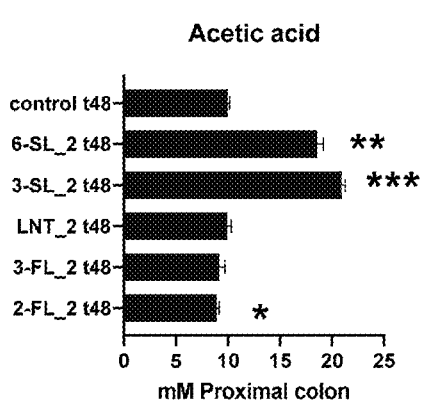
FIG. 9 shows the results from the detection of acetic acid produced in a fecal batch fermentation experiment with each human milk oligosaccharide alone in a simulated infant proximal colon in Example 6 of the present disclosure.

Reference is made to FIG. 9 for the detection results of acetic acid produced by small batch fermentation with each HMO in a simulated proximal colon environment. It can be seen that 3-SL and 6-SL have significantly increased acetic acid after 48 hours of fermentation in the simulated proximal colon. Among them, the effect of 3-SL is more significant.

Figure 10:
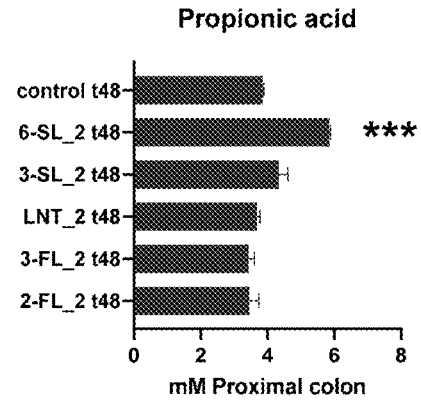
FIG. 10 shows the results from the detection of propionic acid produced in a fecal batch fermentation experiment with each human milk oligosaccharide alone in a simulated infant proximal colon in Example 6 of the present disclosure.

Reference is made to FIG. 10 for the detection results of propionic acid produced by small batch fermentation with each HMO in a simulated proximal colon environment. It can be seen that 6-SL has significantly increased propionic acid after 48 hours of fermentation in the simulated proximal colon.

Figure 11:
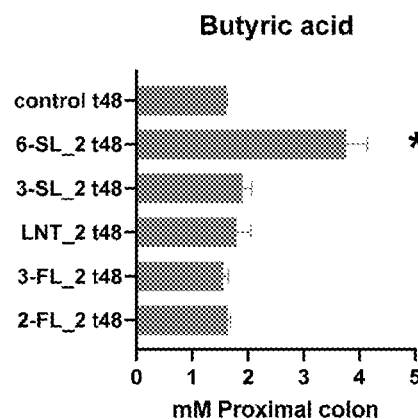
FIG. 11 shows the results from the detection of butyric acid produced in a fecal batch fermentation experiment with each human milk oligosaccharide alone in a simulated infant proximal colon in Example 6 of the present disclosure.

Reference is made to FIG. 11 for the detection results of butyric acid produced by small batch fermentation with each HMO in a simulated proximal colon environment in the present disclosure. It can be seen that in the simulated proximal colon environment, 6-SL can significantly increase the production of butyric acid after 48 hours of fermentation.

Figure 12:
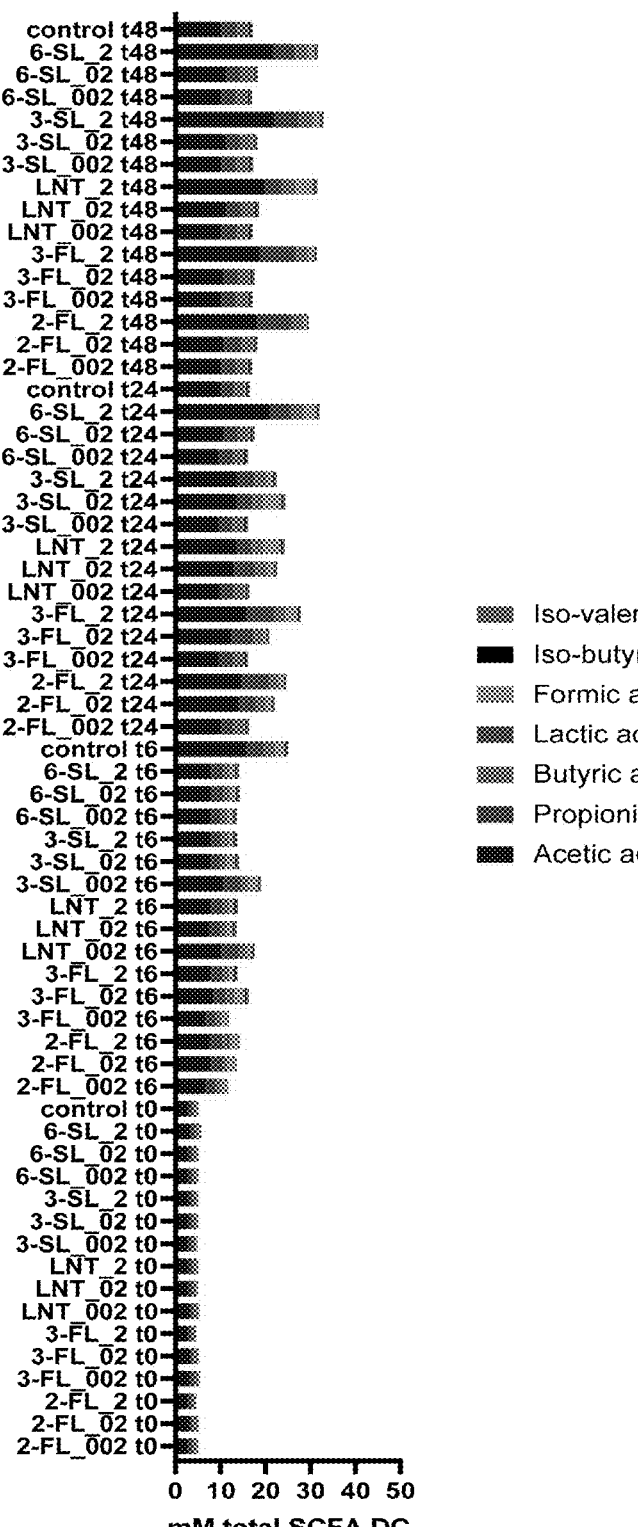
FIG. 12 shows the overall results from the detection of short chain fatty acids produced by small batch fermentation with each HMO in a simulated distal colon environment in Example 7 of the present disclosure.

Example 7: Production of Short Chain Fatty Acids by Small Batch Fermentation with Each HMO in the Simulated Distal Colon Environment Reference is made to FIG. 12 for the total detection results of short chain fatty acids produced by small batch fermentation with each HMO in a simulated distal colon environment. It can be seen that the production of SCFA by each HMO in the distal colon is more active than in the proximal colon, which is also consistent to the generally accepted scientific view that most of the fermentation of the intestinal flora occurs in the distal colon. The SCFA produced increased with time from 0, 6, 24, to 48 hours. At the time point of 6 hours, 0.02 g/L of 3-SL and 0.02 g/L of LNT produced relatively more short chain fatty acids; at the time point of 24 hours, 2 g/L of 6-SL and 2 g/L of 3-FL produced relatively more short chain fatty acids; and at the time point of 48 hours, all HMOs at 2 g/L could produce more short chain fatty acids.

Reference is made to FIG. 13 for the detection results of formic acid produced by small batch fermentation with each HMO in a simulated distal colon environment. It can be seen that all HMOs have significantly increased formic acid after 48 hours of fermentation in the simulated distal colon. Among them, the effects of 3-SL, 6-SL, LNT and 3-FL are more significant.

Reference is made to FIG. 14 for the detection results of acetic acid produced by small batch fermentation with each HMO in a simulated distal colon environment. It can be seen that all HMOs have significantly increased acetic acid after 48 hours of fermentation in the simulated distal colon. Among them, the effects of 3-SL, 6-SL and LNT are more significant.

Reference is made to FIG. 15 for the detection results of propionic acid produced by small batch fermentation with each HMO in a simulated distal colon environment. It can be seen that all HMOs have significantly increased propionic acid after 48 hours of fermentation in the simulated distal colon. Among them, the effects of 3-SL and 3-FL are more significant.

Reference is made to FIG. 16 for the detection results of butyric acid produced by small batch fermentation with each HMO in a simulated distal colon environment. It can be seen that 3-SL and 6-SL have significantly increased butyric acid after 48 hours of fermentation in the simulated distal colon.

Example 8: Production of Butyric Acid by Fermentation with Each HMO in the SHIME Model in the Simulated Distal Colon Environment Reference is made to Table 1 for the detection results of butyric acid produced by the fermentation with each HMO in the SHIME model in the simulated distal colon environment.

TABLE 1

| Short chain fatty acids | Log2 (day 14/day 1) | | | | | |
|---|---|---|---|---|---|---|
| Distal colon | Control | 2'-FL | 3-FL | LNT | 3-SL | 6-SL |
| Butyric acid | −1.18 | −0.67 | −0.33 | −0.70 | −0.13 | −0.66 |

In the case of fermentation in the SHIME model, after 14 days of fermentation, butyric acid produced by each HMO was decreased compared to that on the first day of fermentation, with the control group (without HMO) having the highest ratio of the decrease; the decrease ratio on Day 14 was significantly improved over Day 1 after the HMO intervention. Among them, the decrease ratio with 3-SL was the smallest, followed by 3-FL, with 6-SL, 2'-FL and LNT also showing a good improving effect compared to the control. It can be seen that each HMO has a certain advantage in the regulation of butyric acid in the fermentation product as compared with the control group without HMO.

What is claimed is:

1. A method for reducing the production of isobutyric acid and/or isovaleric acid in the distal colon of an infant, comprising:
administering to the infant in need a food comprising an effective amount of human milk oligosaccharide 2'-fucosyllactose (2'-FL) or 3'-fucosyllactose (3-FL) to reduce the production of isobutyric acid and/or isovaleric acid in the distal colon of the infant", wherein the food is an infant formula powder.

2. The method according to claim 1, wherein the food is used for reducing the production of isobutyric acid in the distal colon; the human milk oligosaccharide is 2'-FL or 3-FL.

3. The method according to claim 2, wherein
the effective amount of 2'-FL used in the food is 14.2 mg/100 g powder to 3182.2 mg/100 g powder in the milk powder, or 0.02 g/L to 4.2 g/L in terms of liquid milk; or
the effective amount of 3-FL used in the food is 14.2 mg/100 g powder to 1515.3 mg/100 g powder in the milk powder, or 0.02 g/L to 2.0 g/L in terms of liquid milk.

4. The method according to claim 1, wherein the food is used for reducing the production of isovaleric acid in the distal colon; the human milk oligosaccharide is 2'-FL or 3-FL.

5. The method according to claim 4, wherein
the effective amount of 2'-FL used in the food is 14.2 mg/100 g powder to 3182.2 mg/100 g powder in the milk powder, or 0.02 g/L to 4.2 g/L in terms of liquid milk; or
the effective amount of 3-FL used in the food is 14.2 mg/100 g powder to 1515.3 mg/100 g powder in the milk powder, or 0.02 g/L to 2.0 g/L in terms of liquid milk.

6. The method according to claim 2, wherein
the effective amount of 2'-FL used in the food is 70.9 mg/100 g powder to 1818.4 mg/100 g powder, or 0.1 g/L to 2.4 g/L in terms of liquid milk; or
the effective amount of 3-FL used in the food is 70.9 mg/100 g powder to 1515.3 mg/100 g powder, or 0.1 g/L to 2.0 g/L in terms of liquid milk.

7. The method according to claim 2, wherein the effective amount of 2'-FL used in the food is 70.9 mg/100 g powder to 1515.3 mg/100 g powder, or 0.1 g/L to 2.0 g/L in terms of liquid milk; or the effective amount of 3-FL used in the food is 70.9 mg/100 g powder to 757.7 mg/100 g powder, or 0.1 g/L to 1.0 g/L in terms of liquid milk.

8. The method according to claim 4, wherein the effective amount of 2'-FL used in the food is 70.9 mg/100 g powder to 1818.4 mg/100 g powder, or 0.1 g/L to 2.4 g/L in terms of liquid milk; or the effective amount of 3-FL used in the food is 70.9 mg/100 g powder to 1515.3 mg/100 g powder, or 0.1 g/L to 2.0 g/L in terms of liquid milk.

9. The method according to claim 4, wherein the effective amount of 2'-FL used in the food is 70.9 mg/100 g powder to 1515.3 mg/100 g powder, or 0.1 g/L to 2.0 g/L in terms of liquid milk; or the effective amount of 3-FL used in the food is 70.9 mg/100 g powder to 757.7 mg/100 g powder, or 0.1 g/L to 1.0 g/L in terms of liquid milk.

\* \* \* \* \*